United States Patent

Katzoff et al.

[11] 3,956,281
[45] May 11, 1976

[54] PREPARATION OF SUBSTITUTED ALDAZINES

[75] Inventors: Lionel Katzoff, Baltimore; Achille Silvestri, Bel Air, both of Md.

[73] Assignee: The United States of America as represented by the Secretary of the Army, Washington, D.C.

[22] Filed: Aug. 7, 1969

[21] Appl. No.: 851,142

[52] U.S. Cl. ........................... 260/240 G; 23/230 R; 252/408; 260/566 B
[51] Int. Cl.² ................ C07D 295/00; C07C 131/00
[58] Field of Search ..................... 260/566 B, 240 G

[56] References Cited
UNITED STATES PATENTS
2,883,423  4/1959  Mosher et al. ................. 260/566 B OTHER PUBLICATIONS
Mosher et al., Talanta, Vol. 15, pp. 482–484, (1968).

*Primary Examiner*—Leland A. Sebastian
*Attorney, Agent, or Firm*—Nathan Edelberg; Robert P. Gibson; Kenneth P. Vanwyck

[57] ABSTRACT

A composition of matter and method of preparation having the formula

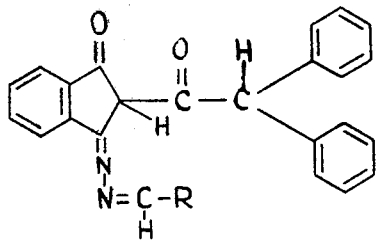

wherein R is

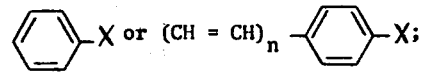

$n$ is an integer from 1 to 4 inclusive; X is selected from $OH, NH_2$, monoalkyl amine, dialkyl amine, aryl amine, $N(R_1)_2$, and combinations thereof; and $R_1$ is an aliphatic radical. The composition is used to detect glycolate compounds.

2 Claims, No Drawings

PREPARATION OF SUBSTITUTED ALDAZINES

DEDICATORY CLAUSE

The invention described herein may be manufactured, used, and licensed by or for the Government for governmental purposes without the payment to us of any royalty thereon.

Our invention relates to composition of matter used to detect glycolate incapacitating chemical agents. Since glycolate incapacitating agents act on the autonomic parasympathetic and central nervous systems, to interfere with transmission of impulses along a nerve or from nerve fibers to muscle fibers or secretory cells or from one nerve fiber to another across synapses in ganglia, and produce incapacitating physiological effects, a need exists to detect the presence of such glycolate agents in the atmosphere; such as could be encountered in field conditions during warfare. The prior art detection techniques, such as electrochemical cell and various spot analysis detection techniques, were all inadequate and presented problems in that they were not sufficiently sensitive, were subject to various interferences, and would not detect all glycolate agents. Our invention was conceived and reduced to practice to overcome the aforementioned prior art problems and to satisfy the long felt need for a universal, effective, and efficient glycolate incapacitating agent detection means.

A principal object of our invention is to provide a means which is sensitive to and will detect all glycolate incapacitating chemical agents.

Another object of our invention is to provide a means which will detect all glycolate incapacitating agents and which will not be subject to any interference by any conditions or matter.

Other objects of our invention will be obvious or will appear from the specification hereinafter set forth.

Our invention involves compositions of matter as glycolate chemical incapacitating agent detection means which are represented by the generic formula as follows:

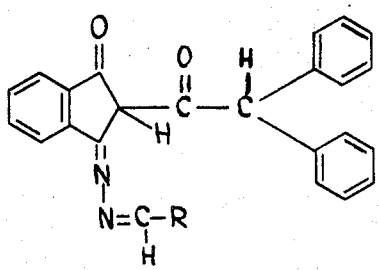

wherein R is a group selected from

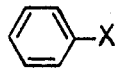

and

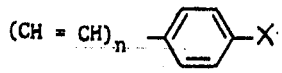

and n is an integer from 1 to 4 inclusive but preferably 1 and 2 and X is a group selected from $OH, NH_2$, monoalkyl amine, dialkyl amine, aryl amine, $N(R_1)_2$, and combinations thereof and $R_1$ is any aliphatic radical but preferably $CH_3$. X can be substituted on the ring in the ortho, meta, and para positions, and the particular X group and the ring position affect the color formation and fluorescence of the glycolate agent-detection composition reaction product complex.

The new composition of matter detection means of our invention were prepared as follows.

EXAMPLE 1

A mixture of 1.75 grams of p-dimethylaminocinnamaldehyde and 2.92 grams of 2-diphenylacetyl-1, 3-indandione-1-hydrazone was stirred to produce a homogeneous mixture and refluxed in 50 ml of chloroform for 20 minutes; two drops of concentrated HCl being added to the reflux mixture prior to refluxing to act as a catalyst. A red solution was produced which was filtered hot to remove any unreacted starting materials. The filtered solution was coold to room temperature and 100–200 ml of anhydrous ether was added which produced a red precipitate. The precipitate was removed from the solution through filtration and recrystallized from 50 ml of a boiling methanol-chloroform (10:1) mixture which yielded 4.61 grams of a brick red solid, 2-diphenylacetyl-1, 3-indandione-1-p-dimethylaminocinnamaldazine, having a melting point of 198°C.

Percent analysis for $C_{34}H_{29}N_3O_2$. Calcd: C,79.8; H, 5.7; N, 8.2; O, 6.3. Found: C, 79.9; H, 5.7; N, 8.5; O, 6.2.

EXAMPLE 2

A mixture of 2.5 grams of N-methiodide-4-pyridine carboxaldehyde and 2.92 grams of 2-diphenylacetyl-1, 3-indandione-1-hydrazone was stirred to produce a homogeneous mixture and refluxed in 50 ml of chloroform for thirty minutes; two drops of concentrated HCl being added to the reflux mixture; prior to refluxing, to act as a catalyst. The refluxed solution was cooled to room temperature, and a brownish orange product began to precipitate on cooling. After cooling to room temperature, 100–200 ml of anhydrous ether was added, and a brownish orange product precipitated. The product was extracted with 50 ml of a hot methanol-chloroform (10:1) mixture. After filtering the mixture while hot, 4.65 grams of a brownish orange solid, 2-diphenylacetyl-1, 3-indandione-1-p-N-methiodidepyridine carboxaldazine was obtained which had a melting point of 230°C.

Percent analysis for $C_{30}H_{20}IN_3O_2$. Calcd: C, 62,0; H, 3.5; I, 21.8; N, 7.5; O, 5.5. Found: C, 61.5; H, 4.3; I, 21.7; N, 7.1; O, 5.0.

A prior art composition of matter which we found to be a detection mens for glycolate incapacitating chemical agents is 2-diphenylacetyl1, 3-indandione-1-p-dimethylaminobenzaldazine; the composition being reported by R. A Braun and W. A. Mosher in the *Journal of the American Chemical Society*, 80, 3048–50 (1958).

The efficacy of our compositions of matter and technique were tested as follows.

EXAMPLE 3

10 milligrams of detection composition means of 2-diphenylacetyl-1, 3-indandione-1-p-N methiodidepyridine carboxaldazine was dissolved in 10 milliliters of tetrahydrofuran acidified with 2–3 drops of concentrated HCl. Glycolate incapacitating chemical agent was spotted as an ethanolic solution on the grid side of a conventional Gelman glass microfiber sheet. The detection composition means was sprayed as a very fine mist onto the glycolate spotted grid side. Upon viewing the microfiber sheet, as soon as the solvent had volatilized (1–2 minutes), under either long or short wave ultra violet light, the long wave being generally more sensitive, yellow fluorescent spots were visible which demonstrated the presence of glycolate incapacitating agent. As a result of our testing, we determined that the presence of as little as 0.5 micrograms of glycolate incapacitating agent can be detected by our method. The detection composition can be sprayed by either a Freon propelled spray can or by an air driven spray; both spray techniques being those as conventionally used in thin layer chromatography. In the case of the Freon spray can, a three ounce can was used which contained 20 grams of detection composition of our invention, 40 grams of trichloromonofluoromethane, and 40 grams of dichlorodifluoromethane.

EXAMPLE 4

10 milligrams of detection composition means 2-diphenylacetyl-1, 3-indandione-1-p-dimethylaminocinnamaldazine was dissolved in 30 milliliters of glacial acetic acid to which 0.65 ml of concentrated HIl was added. Glycolate incapacitating chemical agent was spotted as an ethanolic solution on the grid side of a conventional Gelman glass microfiber sheet. The detection composition means was sprayed onto the Glycolate spotted grid side as described above in Example 3. The microfiber sheet was viewed with ultra violet light, as in Example 3, and a reddish-orange fluorescence was visible which demonstrated the presence of glycolate incapacitating agent.

While the glycolate incapacitating agent was sprayed on for test purposes, samples can be collected on any substrate and by any conventional sampling means to be tested by our technique and detection compositions for the presence of glycolate agent. Also, while we utilized acidified tetrahydrofuran and acetic/HCl acid as solvents, it is readily apparent that a variety of equivalent solvent systems based on other aqueous and/or organic solvents with suitable acids would be obvious to one of ordinary skill in the art.

We wish it to be understood that we do not desire to be limited to the exact details shown and described, for obvious modifications will occur to a person skilled in the art.

We claim:

1. A method of preparing 2-diphenylacetyl-1, 3-indandione-1-p-dimethylaminocinnamaldazine comprising the steps of preparing a mixture by mixing 1.75 grams of p-dimethylaminocinnamaldehyde with 2.92 grams of 2-diphenylacetyl-1, 3-indandione-1-hydrazone; stirring the mixture to produce a homogeneous mixture; adding 50 ml of chloroform and approximately 2 drops of concentrated HCl to the homogeneous mixture to form a solution, said HCl being adapted to act as a catalyst; refluxing the chloroform-homogeneous mixture solution for approximately 20 minutes, filtering the refluxed solution while hot to remove any unreacted starting materials; cooling the filtered solution to room temperature; adding 100 to 200 ml of anhydrous ether to the cooled solution to produce a red precipitate; filtering the cooled solution to separate the precipitate; and recrystallizing the precipitate from 50 ml of a boiling methanol-chloroform mixture to produce a product having a melting point of 198°C, said methanol-chloroform mixture being in the ratio of 10:1 respectively.

2. A method of preparing 2-diphenylacetyl-1, 3-indandione-1-p-N-methiodidepyridine carboxaldazine comprising the steps of preparing a mixture by mixing 2.50 grams of N-methiodide-4-pyridine carboxaldehyde with 2.92 grams of 2-diphenylacetyl-1, 3-indandione-1-hydrazone; stirring the mixture to produce a homogeneous mixture; adding 50 ml of chloroform and approximately two drops concentrated HCl to the homogeneous mixture to form a solution, said HCl being adapted to act as a catalyst; refluxing the chloroform-homogeneous mixture solution for approximately thirty minutes; cooling the refluxed solution to room temperature; adding 100 to 200 ml of anhydrous ether to the cooled refluxed solution to produce a brownish orange precipitate; adding 50 ml of a hot methanol-chloroform mixture to the ether-cooled refluxed solution to extract the precipitate, said methanol-chloroform mixture being in the ratio of 10:1 respectively; filtering the methanol-chloroform-ether refluxed solution while hot to produce a product having a melting point of 230°C.

* * * * *